United States Patent [19]

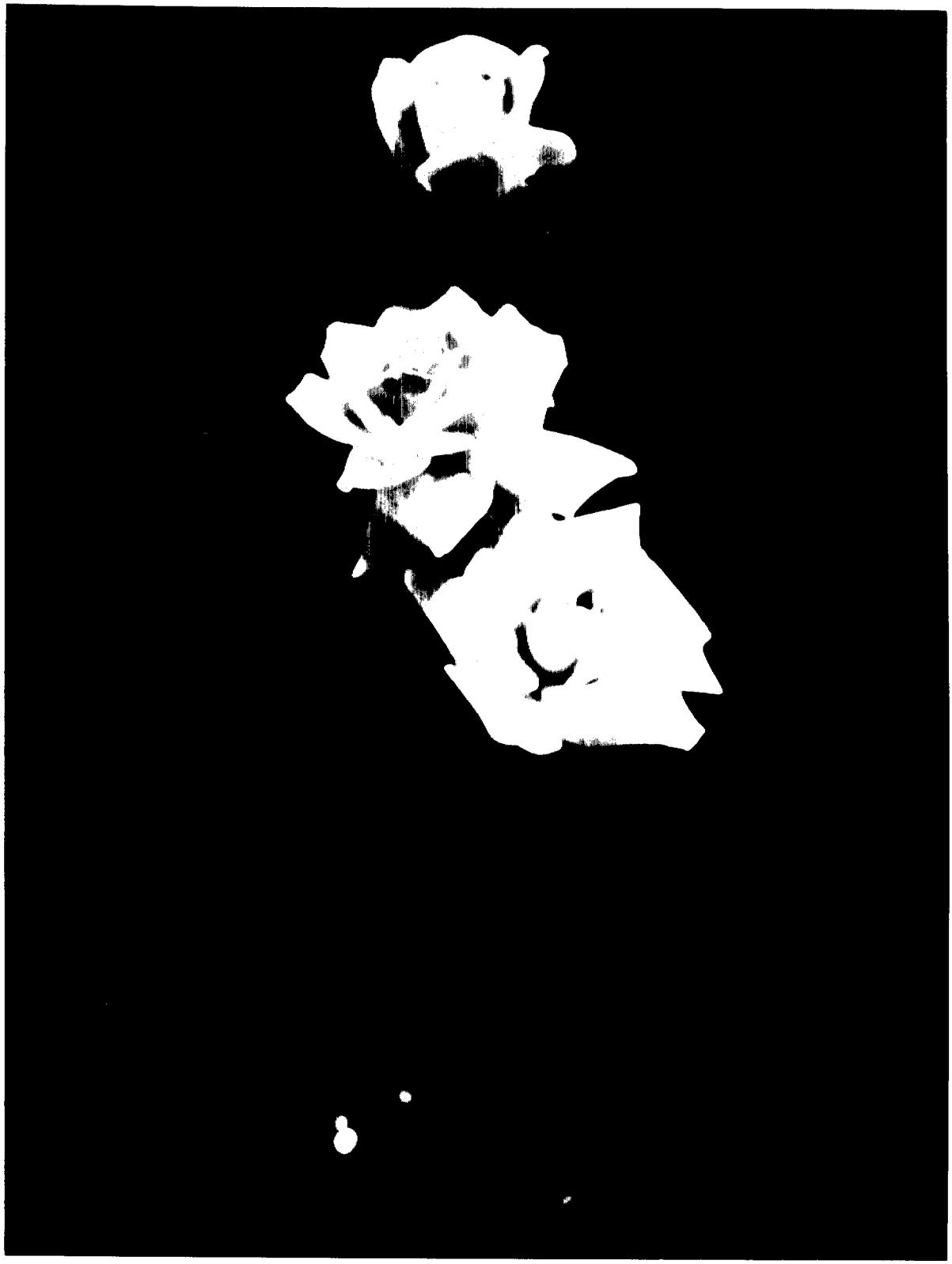

Jolly

[11] Patent Number: Plant 5,728

[45] Date of Patent: Apr. 29, 1986

[54] ROSE PLANT

[75] Inventor: Nelson F. Jolly, Galena, Md.

[73] Assignee: Jolly's Rosehill Farm of Kent, Inc., Galena, Md.

[21] Appl. No.: 663,465

[22] Filed: Oct. 18, 1984

[51] Int. Cl.[4] ..... A01H 5/00

[52] U.S. Cl. ..... Plt./9

[58] Field of Search ..... Plt./9

*Primary Examiner*—Robert E. Bagwill

*Attorney, Agent, or Firm*—Vincent G. Gioia

[57] ABSTRACT

A new miniature rose variety of the light red, deep pink coloring class of good form and substance.

1 Drawing Figure

The present invention relates to a new and distinct variety of rose plant of the miniature rose class, which was originated by my crossing as seed parent the rose known as "Operetta" and the rose known as "Bonny" as pollen parent. The varietal denomination of this new variety is "Pink Triumph".

Among the novel characteristics possessed by this new variety which distinguish it from its parents and all other varieties of which I am aware are its well formed, heavily petaled flowers of good exhibition form and substance which open into symmetrical light red, deep pink bloom. In the ⅓ to ½ open stages flowers combine deeper toned red-pink coloring where petals bunch with lighter colored outer petals. Asexual reproduction by budding of the new variety as performed in Kent County, Md., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.) The terminology used in color description herein refers to plate numbers in the aforementioned color chart, e.g., "52A" is plate 52A of The Royal Horticultural Society Colour Chart.

Parentage: Seedling.

*Seed parent.*—"Operetta".

*Pollen parent.*—"Bonny".

Class: Miniature.

The following observations are made of specimens grown outdoors in Kent County, Md., during the month of August.

1. FLOWER

Blooming habit: Continuous.

A. Bud:

(1) *Size.*—Medium.

(2) *Form.*—Long pointed.

(3) *Color.*—When sepals first divide — near 52A lightening to 52D.

(4) *Sepals.*—Longer than bud.

(5) *Peduncle.*—Length — 1 to 1½ inches. Aspect — Straight. Strength — Erect. Color — Near 138A.

B. Bloom:

(1) *Size.*—Average size when fully expanded — about 1½ to 1¾ inches.

(2) *Borne.*—Primarily one to a stem.

(3) *Form.*—High centered at first, becoming flat, some petals reflex to quills upon opening; others roll under; flower maintains symmetrical exhibition form until center is lost.

(4) *Petalage.*—Number of petals under normal conditions — About 46 to 50.

(5) *Color.*—As sepals fall, first color shown appears Carmine rose, near 52A, but bud coloring quickly lightens to Spinel red 54C. Some deeper-toned, 48A to B, appears in veining or washing in petal undersurface and is more pronounced as flowers open. The deeper-toned color is very visible where petals bunch and in ⅓ to ½ open stages, the flowers display a combination of Neyron rose, near 55D to 56A, coloring of outer petals and deeper-toned 48A to B flower centers. The deeper tonality becomes less visible as flowers open further.

C. Petals:

(1) *Texture.*—Thick, good substance.

(2) *Appearance.*—Inside — velvety, outside — velvety.

(3) *Form.*—Rounded, point at apex.

(4) *Arrangement.*—Regularly arranged, shingle-like.

(5) *Petaloids in center.*—Medium.

(6) *Persistence.*—Petals tend to retain.

(7) *Fragrance.*—Slight.

(8) *Lasting quality.*—Very long lasting on plant and as cut flower.

2. REPRODUCTIVE ORGANS

A. Stamens, filaments and anthers:

(1) *Arrangement.*—Regularly arranged around styles.

(2) *Color.*—Near 16B.

B. Pollen:

*Color.*—Near 15A.

C. Styles: Uneven, medium length.

D. Stigmas:

*Color.*—Near 55C.

E. Hips:

*Shape.*—Globular.

*Size.*—Medium.
*Color.*—Orange.
*Do seeds protrude?* -No.

3. PLANT

A. Form: Upright, compact.
B. Growth: Very vigorous, uniform branching.
*Height attained.*—About 24 to 26 inches.
C. Foliage: Compound 5 to 7 leaflets.
(1) *Size.*—Medium.
(2) *Quantity.*—Abundant.
(3) *Color.*—New foliage: Upper side — Near to 148B tinged with near 46A. Under side — Near to 148C tinged with near 47A. Old foliage: Upper side — Near 139A. Under side — Near 191A.
(4) *Shape.*—Oval, pointed.
(5) *Texture.*—Upper side is smooth, shiny and under side is matte.
(6) *Edge.*—Serrated.
(7) *Serration.*—Serrate.
(8) *Leaf stem.*—Color — Near to 138B. Under side — Near 138B.
(9) *Stipules.*—Medium, short, pointed.

(10) *Resistance to disease.*—Blackspot — Average. Mildew — Average.
D. Wood:
(1) *New wood.*—Color — Near 166A. Bark — Smooth.
(2) *Old wood.*—Color — Near 138A. Bark — Smooth.
E. Thorns:
(1) *Thorns.*—Quantity (main stalk): ordinary. On laterals from stalk — Few. Form — hooked. Length — Medium. Color — Near 45D. Position — Irregular.
(2) *Prickles.*—Few.
F. Winter hardiness: Winter hardy.

I claim:

1. A new and distinct variety of rose plant of the miniature rose class, substantially as shown and described, characterized particularly by well formed, heavily petalled flowers of light Neyron rose coloring having deeper-toned flower centers where petals remain bunched until opening and with petals reflexing and rolling under upon opening while retaining good form.

* * * * *